United States Patent [19]
Byatt et al.

[11] Patent Number: 6,136,562
[45] Date of Patent: Oct. 24, 2000

[54] BOVINE PLACENTAL LACTOGEN

[75] Inventors: John C. Byatt, Grover; Scott D. Hauser, Webster Groves; Gwen G. Krivi, St. Louis, all of Mo.; Ned R. Siegel, Belleville, Ill.; Christine E. Smith, St. Louis; Jeannine M. Stafford, Ballwin, both of Mo.

[73] Assignee: Monsanto Company, St. Louis, Mo.

[21] Appl. No.: 07/979,361

[22] Filed: Nov. 20, 1992

Related U.S. Application Data

[63] Continuation of application No. 07/221,124, Jul. 21, 1988, abandoned, which is a continuation-in-part of application No. 07/092,116, Sep. 2, 1987, abandoned.

[51] Int. Cl.$^7$ .............................. C12N 15/00; C12N 1/21; C12Q 1/68; C07H 21/04
[52] U.S. Cl. .................. 435/69.4; 435/252.3; 435/254.2; 435/320.1; 435/325; 536/23.51
[58] Field of Search ................................ 435/69.4, 172.3, 435/240.1, 240.2, 252.3, 252.33, 320.1, 325, 254.2; 536/23.51

[56] References Cited

U.S. PATENT DOCUMENTS

| | | | |
|---|---|---|---|
| 4,554,256 | 11/1985 | Sasser et al. | 436/510 |
| 4,675,297 | 6/1987 | Baxter et al. | 435/253 |
| 4,725,549 | 2/1988 | Cooke et al. | 435/243 |
| 4,767,711 | 8/1988 | Schuler et al. | 435/243 |
| 5,010,011 | 4/1991 | Schuler et al. | 435/252.3 |

FOREIGN PATENT DOCUMENTS

| | | |
|---|---|---|
| 8600338 | 1/1988 | WIPO . |

OTHER PUBLICATIONS

Suggs et al *Proc. Natl Acad. Sci.* Nov. 1981 vol. 78 (11) pp 6613–6617 "Use of synthetic oligonucleotides as hybridization probes: Isolation of cloned cDNA sequences for human $\beta_2$–microglobulin".
Arima et al. (1986) Endocinology 113: 2186–2194.
Eakle et al. (1982) Endocinology 110: 1758–1765.
Murthy et al. (1982) Endocrinology 111: 2117–2124.
Byatt et al. (1986) Endocrinology 119: 1343–1350.
Bolander et al. (1976) J. Biol. Chem. 251: 2703–2706.
Shimomura (1984) Masters Thesis, Univ. Wisconsin–Madison.
Duello et al. (1986) Endocrinology 119: 1351–1355.
Byatt and Bremel (1986) S. Dairy Sci. 69: 2066–2071.
Schellenberg et al. (1982) Endocrinology 111: 2125–2128.
Buttle et al. (1976) Endocrinology 68: 141–146.
Newnham et al. (1986) Placenta 7: 51–64.
Chan et al. (1986) Endocrinology 119: 2623–2628.
Newnham et al (1986) Am. J. Obstet. Gynecol 154: 663–666.
Emane et al. (1986) Endocrinology 118: 695–700.
Freemark et al. (1985) Endocrinology 116: 1275–1280.
Waters et al. (1985) J. Endocr. 106: 377–386.
Servely et al. (1983) Gen. and Comp. Endocr. 51: 255–262.
Rüsse et al. (1984) J. Endocr. 102: 121–130.
Freemark et al. (1983) Endocrinology 112: 402–404.
Butler et al (1981) J. Animal Sci 53: 1077–1081.
Hayden et al. (1980) J. Endocr. 86: 279–290.
Hayden et al. (1979) J. Dairy Sci. 62: 53–57.
Lowe et al. (1979) Am. J. Obstet. Gynecol. 135: 773–777.
Buttle et al. (1978) J. Endocr. 77: 59p.
Chan et al. (1978) Endocrinology 102: 632–640.
Martal et al. (1978) Endocrinology 103: 193–199.
Hurley et al. (1977) Endocrinology 101: 1635–1638.
Martal et al. (1977) J. Biochemistry 8: 415–417.
Albert L. Lehninger, Principles of Biochemistry (1982), p. 898.
Schuler et al. Biochemistry 1988, 27, 8443–8448.
Schuler et al. PNAS 84: 5650–5654 1987.

*Primary Examiner*—Robert A. Schwartzman
*Assistant Examiner*—Andrew Wang
*Attorney, Agent, or Firm*—Gary M. Bond, Esq.; Howrey Simon Arnold & White, LLP

[57] ABSTRACT

This invention relates to bovine placental lactogen, amino acid sequences thereof, DNA sequences coding therefor, its production by synthetic means and its use to produce a biological response in cattle.

26 Claims, 4 Drawing Sheets

| | | |
|---|---|---|
| 1 | CGCTCGCCCCGGCTCCCTCTCGCTGCTTTTGTCTCTCGGGCGTGCCTCTCCCCACCTCC | 60 |
| 61 | GATTTGCTACACTAAGGCTCCGTCAATGGACTGCATTGAGAGCCGGCTCCGGCGCGAGT | 120 |
| 121 | GCCTCTCCGCTTCACGCTCTGATTTCCAGGCATTCTTCCCTTATTAAGTATTCGTGTAATA | 180 |
| 181 | TTAATAGTCATGAATATCTGCTATTAGGAGGCTCCAGGAACGCTGCCCAGCGCGGTTATT | 240 |
| 241 | AGAAGCTCAAGGCGAAGCGCGGCTCAGAAAAGAGGGGAGACACGGATTAAGGAACACGC | 300 |
|   | * |   |
| 301 | GCGGTTGGGCCATCTCCCCATCAGCAGCAGTCCTCATCCTCTGGGATTTCTCTCCAATCCTC | 360 |
| 361 | ATGGCTCCAGCATCTAGCCATCGTGGGCACCAGTGGGATTTGTGACCTTGTTGAGGGTCC | 420 |
|   | MetAlaProAlaSerSerHisArgGlyHisGlnTrpIleCysAspLeuValArgGlySer |   |
| 421 | TGCCTGCTCCTGCTGCTGGTGTCAAATCTACTCTTGTGCCAGGGTG<u>C</u>GGAGGATTAT | 480 |
|   | CysLeuLeuLeuLeuLeuValValSerAsnLeuLeuLeuCysGlnGlyAlaGluAspTyr |   |
|   |                                              Val |   |
| 481 | GCACCATACTGTAAAAACCAACTGGCAACTGCCGGATTCCCCTTCAAAGCCTGTTTGAG | 540 |
|   | AlaProTyrCysLysAsnGlnProGlyAsnCysArgIleProLeuGlnSerLeuPheGlu |   |

FIG. 1A

541  AGAGCAACATTGGTGGCTAGCAACAACTATAGGCTCGCCAGGGAAATGTTCAATGAATTT    600
     ArgAlaThrLeuValAlaSerAsnAsnTyrArgLeuAlaArgGluMetPheAsnGluPhe

601  AATAAACAGTTTGGGCGAGGGCAAAACTTCACTTCCAAGGTCATCAACAGCTGCCACACC    660
     AsnLysGlnPheGlyGluGlyLysAsnPheThrSerLysValIleAsnSerCysHisThr

661  GAATTCATGACTACCCCTAACAACAAAGAAGCAGTGCAAATACAGAGGACGAAGCCCTG    720
     GluPheMetThrThrProAsnAsnLysGluAlaAlaAsnThrGluAspGluAlaLeu

721  TTGAGGTTGGTTATCAGTTTGCTCCACTCGTGGATGAACCTCTGCATCAGGCAGTCACA    780
     LeuArgLeuValIleSerLeuLeuHisSerTrpAspGluProLeuHisGlnAlaValThr

781  GAGTTGTTGCACAGGAATGGAGCCTCACCTGATATCTTGGCAAGGCTAAAGAGATTGAG    840
     GluLeuLeuHisArgAsnGlyAlaSerProAspIleLeuLeuAlaArgAlaLysGluIleGlu

841  GACAAGACCAAAGTACTTCTAGAGGTGTGGAAATGATACAAAAAGGGTTCATCCTGGA    900
     AspLysThrLysValLeuLeuGluValValGluMetIleGlnLysArgValHisProGly

901  GAGAAGAAGAACGAGCCTATCCAGTGTGGTCAGAAAAGTCCTCCCTGACAGCAGACGAT    960
     GluLysLysAsnGluProIleGlnCysGlyGlnLysSerProProAspSerSerLeuThrAlaAspAsp

FIG. 1B

```
 961  GAGGATGTGGCGCCAAACTGCCTTTATAGAATGTTCCACTGCTACACAGGATTCGAGT  1020
      GluAspValArgGlnThrAlaPheTyrArgMetPheHisCysLeuHisArgAspSerSer

1021  AAAATTAGCACCTACATCAATTTGCTTAAGTGCCGATTCACCCCATGCTAAGCCCACAAT  1080
      LysIleSerThrTyrIleAsnLeuLeuLysCysArgPheThrProCys- - -

1081  TAACCCAACCAGTCCTGAGATGGTTAGTGATGATCATCCCGTCAAAAGCTTCTTTGAGT  1140

1141  TTTATAGCTCTTTAATYGCATGTTTGGGTGTAATGGGTTCTATCTGAAACAAAATAAACA  1200

1201  CAGATTCTGTAGAGATGTCAAAATCTAAAAAAAAAAAAAAAAAAAAAAAAAAAAA...
```

FIG. 1C

CLONE A
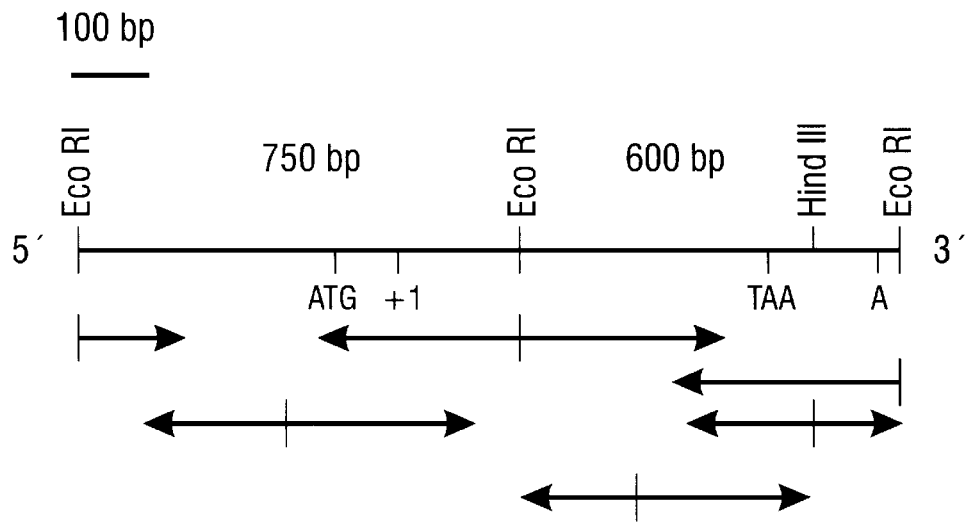
CLONE B
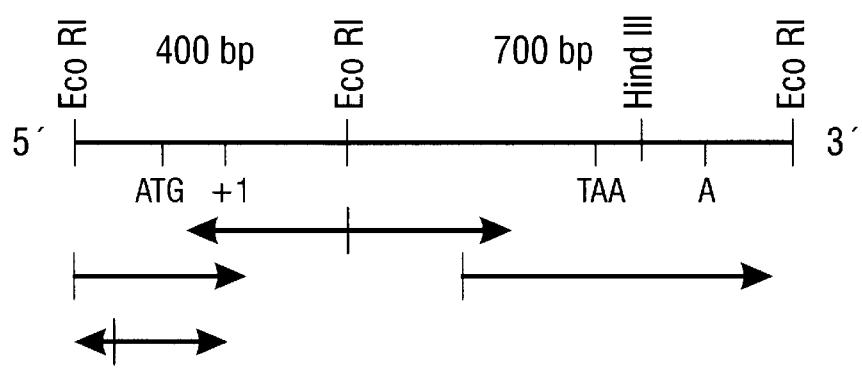
FIG. 2

BOVINE PLACENTAL LACTOGEN

CROSS REFERENCE TO RELATED APPLICATIONS

This application is a continuation of 07/221,124, filed Jul. 21, 1998, now abandoned, which is a continuation-in-part of 07/092,116, filed Sep. 2, 1987, now abandoned.

This invention relates to bovine placental lactogen, to its production by biosynthetic means and to its use to produce a biological response in cattle.

Placental lactogen is a peptide of the growth hormone gene family. Somatotropin (growth hormone) can increase growth, can increase feed efficiency, can increase milk production, can increase the lean to fat ratio of the animal and can produce other biological responses, depending upon the dosage and when the somatotropin is administered in the lifecycle of the animal. Placental lactogen can produce a variety of biological responses similar to those of somatotropins as well as other biological responses. The evidence to support this range of activity of placental lactogen varies from species to species, with the clearest evidence being in the ovine species, with indications of activity in bovine species as well. This activity makes bovine placental lactogen an attractive candidate for exogenous application to cattle, due to its ability to produce a variety of desirable responses, based on its dose and time of application.

A number of references have discussed purification and characterization of naturally occurring bovine placental lactogen from bovine placentas. See, for instance, Byatt et al., (1986); Arima et al., (1983); Murthy et al., (1982); and Eakle et al., (1982). Although a preliminary analysis of bovine placental lactogen isolated from bovine placentas suggested the presence of at least two allelic forms of bovine placental lactogen, a complete characterization of the bovine placental lactogen species was absent due to an inability to obtain a complete separation of the molecules. The putative allelic variants of bovine placental lactogen were merely isolated as a mixture of proteins and no teaching was made as to how or if the allelic forms could be separated from one another. Indeed, isolation of bovine placental lactogen from placentas is not a practical method for production of sufficiently large quantities or substantially pure quantities for commercial use.

Production of commercial quantities of bovine placental lactogen will only be practical when it becomes possible to synthesize bovine placental lactogen outside of the cow. Common synthetic schemes include chemical synthesis; expression in genetically transformed eucaryotic cells such as by cell culture of genetically transformed mammalian cells or fermentation of genetically transformed yeast cells which contain DNA sequences coding for bovine placental lactogen, along with the appropriate control segments of DNA to allow for expression of the bovine placental lactogen; and expression in genetically transformed procaryotes containing DNA sequences which code for bovine placental lactogen, along with the appropriate control segments of DNA to allow for expression of the bovine placental lactogen. In order to use any of these synthetic schemes, the amino acid sequence of the bovine placental lactogen must be known. In the case of chemical synthesis, the complete amino acid sequence is used directly in the chemical synthesis. In the cases of production by genetically transformed cells, the amino acid sequence is used indirectly by allowing isolation or production of a DNA sequence coding for the bovine placental lactogen so that such a DNA sequence can be inserted into host cells. The complete amino acid sequence of any of the bovine placental lactogen molecules have heretofor not been reported.

This invention fills that gap by providing the complete amino acid sequence for two allelic forms of bovine placental lactogen, which sequences allow for synthetic production of the bovine placental lactogen and for use of that synthetic bovine placental lactogen to produce the biological responses discussed above. Indeed, as described more fully herein, the present invention provides the complete amino acid sequence of two allelic forms of bovine placental lactogen. This discovery is significant as it now provides the means for producing commercial quantities of each allelic species in substantially pure form and means for fully characterizing the biological functions of bovine placental lactogen.

SUMMARY OF THE INVENTION

This invention provides for a composition comprising mature bovine placental lactogen, which is a peptide having substantially the following amino acid sequence, reading from the amino terminus to the carboxy terminus: X-Glu-Asp-Tyr-Ala-Pro-Tyr-Cys-Lys-Asn-Gln-Pro-Gly-Asn-Cys-Arg-Ile-Pro-Leu-Gln-Ser-Leu-Phe-Glu-Arg-Ala-Thr-Leu-Val-Ala-Ser-Asn-Asn-Tyr-Arg-Leu-Ala-Arg-Glu-Met-Phe-Asn-Glu-Phe-Asn-Lys-Gln-Phe-Gly-Glu-Gly-Lys-Asn-Phe-Thr-Ser-Lys-Val-Ile-Asn-Ser-Cys-His-Thr-Glu-Phe-Met-Thr-Thr-Pro-Asn-Asn-Lys-Glu-Ala-Ala-Ala-Asn-Thr-Glu-Asp-Glu-Ala-Leu-Leu-Arg-Leu-Val-Ile-Ser-Leu-Leu-His-Ser-Trp-Asp-Glu-Pro-Leu-His-Gln-Ala-Val-Thr-Glu-Leu-Leu-His-Arg-Asn-Gly-Ala-Ser-Pro-Asp-Ile-Leu-Ala-Arg-Ala-Lys-Glu-Ile-Glu-Asp-Lys-Thr-Lys-Val-Leu-Leu-Glu-Gly-Val-Glu-Met-Ile-Gln-Lys-Arg-Val-His-Pro-Gly-Glu-Lys-Lys-Asn-Glu-Pro-Tyr-Pro-Val-Trp-Ser-Glu-Lys-Ser-Ser-Leu-Thr-Ala-Asp-Asp-Glu-Asp-Val-Arg-Gln-Thr-Ala-Phe-Tyr-Arg-Met-Phe-His-Cys-Leu-His-Arg-Asp-Ser-Ser-Lys-Ile-Ser-Thr-Tyr-Ile-Asn-Leu-Leu-Lys-Cys-Arg-Phe-Thr-Pro-Cys, wherein X is either Ala or Val and which peptide is free from other proteins or peptides of bovine origin.

This invention also provides a composition comprising pre-bovine placental lactogen having a signal peptide at the N-terminus of bovine placental lactogen sequence, resulting in a peptide having substantially the following amino acid sequence, reading from the amino terminus to the carboxy terminus: Met-Ala-Pro-Ala-Ser-Ser-His-Arg-Gly-His-Gln-Trp-Ile-Cys-Asp-Leu-Val-Arg-Gly-Ser-Cys-Leu-Leu-Leu-Leu-Leu-Val-Val-Ser-Asn-Leu-Leu-Leu-Cys-Gln-Gly-X-Glu-Asp-Tyr-Ala-Pro-Tyr-Cys-Lys-Asn-Gln-Pro-Gly-Asn-Cys-Arg-Ile-Pro-Leu-Gln-Ser-Leu-Phe-Glu-Arg-Ala-Thr-Leu-Val-Ala-Ser-Asn-Asn-Tyr-Arg-Leu-Ala-Arg-Glu-Met-Phe-Asn-Glu-Phe-Asn-Lys-Gln-Phe-Gly-Glu-Gly-Lys-Asn-Phe-Thr-Ser-Lys-Val-Ile-Asn-Ser-Cys-His-Thr-Glu-Phe-Met-Thr-Thr-Pro-Asn-Asn-Lys-Glu-Ala-Ala-Ala-Asn-Thr-Glu-Asp-Glu-Ala-Leu-Leu-Arg-Leu-Val-Ile-Ser-Leu-Leu-His-Ser-Trp-Asp-Glu-Pro-Leu-His-Gln-Ala-Val-Thr-Glu-Leu-Leu-His-Arg-Asn-Gly-Ala-Ser-Pro-Asp-Ile-Leu-Ala-Arg-Ala-Lys-Glu-Ile-Glu-Asp-Lys-Thr-Lys-Val-Leu-Leu-Glu-Gly-Val-Glu-Met-Ile-Gln-Lys-Arg-Val-His-Pro-Gly-Glu-Lys-Lys-Asn-Glu-Pro-Tyr-Pro-Val-Trp-Ser-Glu-Lys-Ser-Ser-Leu-Thr-Ala-Asp-Asp-Glu-Asp-Val-Arg-Gln-Thr-Ala-Phe-Tyr-Arg-Met-Phe-His-Cys-Leu-His-Arg-Asp-Ser-Ser-Lys-Ile-Ser-Thr-Tyr-Ile-Asn-Leu-Leu-Lys-Cys-Arg-Phe-Thr-Pro-Cys, wherein X is either Ala or Val and which peptide is free from other proteins or peptides of bovine origin.

In another aspect, this invention provides for structural genes which code for the peptides identified above and for recombinant procaryotic and eucaryotic expression vectors containing those structural genes. The procaryotic expression vector contains upstream from the structural gene a procaryotic promotor and ribosome binding site; and the 5' end of the structural gene, a translation start codon; and downstream from the structural gene, a translation stop codon and a transcription termination signal. The eucaryotic expression vector contains, upstream from the structural gene, a eucaryotic promoter and translation control elements; at the 5' end of the structural gene, a translation start codon; and downstream from the structural gene, a translation stop codon and a 3'-nontranslated polyadenylation transcription termination signal. This invention also provides for genetically transformed eucaryotes comprising the eucaryotic expression vectors described above and for genetically transformed procaryotes comprising the procaryotic expression vectors described above.

This invention also provides methods for production of bovine placental lactogen by chemical synthesis; by expression in genetically transformed eucaryotic cells such as by cell culture of genetically transformed mammalian cells or fermentation of genetically transformed yeast, which contains the eucaryotic expression vector described above; and by expression in genetically transformed procaryotes which contain the procaryotic expression vector described above.

In another aspect, this invention also provides for use of the bovine placental lactogen described above by administration to an animal of an effective amount of bovine placental lactogen to achieve the desired biological response. Preferred methods of administration include parenteral administration such as subcutaneous or intramuscular injection; and administration across bodily membranes, such as intramammary infusion.

BRIEF DESCRIPTION OF THE FIGURES

In the following diagrammatic representations the nucleic acid sequences are provided in a 5' to 3' orientation unless otherwise noted. The nucleotides adenine, guanine, cytosine and thymine are denoted A, G, C and T, respectively. The 20 amino acids are denoted:

| | |
|---|---|
| Ala = alanine | Leu = leucine |
| Arg = arginine | Lys = lysine |
| Asn = asparagine | Met = methionine |
| Asp = aspartic acid | Phe = phenylalanine |
| Cys = cysteine | Pro = proline |
| Gln = glutamine | Ser = serine |
| Glu = glutamic acid | Thr = threonine |
| Gly = glycine | Trp = tryptophan |
| His = histidine | Tyr = tyrosine |
| Ile = isoleucine | Val = valine |

FIG. 1 depicts double-stranded (ds) DNA sequences containing coding sequences for the two allelic forms of bovine placental lactogen (bPL). The numbers refer to the nucleotides and are provided for diagrammatic purposes only. The subscript letters designate the amino acid sequence of bPL encoded in the dsDNA, wherein the underlined amino acids denote the signal peptide ("pre") sequence.

The hatched box denotes an N-linked glycosylation site. The circled amino acid and nucleotides denote the amino acid and nucleotide substitutions, respectively, which differentiate and define the two allelic forms of bPL. The asterisk (*) denotes the start of the bPL messenger RNA encoding the allelic form of bPL containing the amino acid Val and nucleotide substitutions T, T and A noted.

FIG. 2 depicts the restriction maps of two cDNA clones, A and B, encoding bPL. Only relevant restriction sites are shown and approximate base pair (bp) lengths of relevant fragments given. The directional arrows denote the regions of the cDNA's subjected to DNA sequence analysis. "ATG" denotes the start of the pre-bPL protein. "+1" denotes the start of the mature bPL protein. "TAA" denotes a stop codon and "A" denotes the start of the poly A tail.

DETAILED DESCRIPTION OF THE INVENTION

As used herein, the symbols representing amino acids (e.g. Ala for alanine) are those conventionally employed unless otherwise noted, see Lehninger (1976). As used herein, the phrase "free from other proteins or peptides of bovine origin" means free from proteins of native (e.g. bovine) origin. The phase "substantially pure" means that the composition does not contain any other proteins or peptides that materially or adversely affect the biological activity of the bovine placental lactogen. The term "synthetic" means made by means requiring some human manipulation such as, but not limited to, chemical synthesis, enzymatic synthesis and conventional recombinant DNA techniques (see e.g. Maniatis et al., 1982). As used in reference to both the procaryotic and eucaryotic expression vectors, the phrase "at the 5' end of the structural gene" means either within the structural gene at its 5' end or immediately adjacent to the codon at the 5' end of the structural gene.

The present invention provides amino acid sequences for both the mature forms of bovine placental lactogen (bPL) and for pre-bovine placental lactogen (pre-bPL). Pre-bPL refers to the intracellular form of bovine placental lactogen and bPL refers to the mature, secreted (extracellular) form of bovine placental lactogen. Specifically, "pre-bPL" comprises mature bPL with an N-terminal signal peptide sequence.

The present invention also provides DNA sequences encoding mature and pre-bPLs and provides methods and compositions for administering the proteins of the present invention to animals to produce growth promoting effects such as, but not limited to, enhanced growth of bovine mammary parenchyma.

The discovery of the complete amino acid sequence of bPL, pre-bPL and the allelic forms thereof provides a basis for production of peptides having bPL activity in commercial quantities. Such production is carried out by any available process. For example, conventional peptide synthesizing equipment or chemical synthesis is employed.

Alternatively, the herein described amino acid sequences of bPL and pre-bPL allow for the creation (e.g. by chemical and/or enzymatic synthesis) or isolation of DNA sequences encoding bPL and/or pre-bPL. Such DNA sequences are, in turn, useful in creating eucaryotic and procaryotic expression vectors able to produce bPL and/or pre-bPl by recombinant DNA techniques. Furthermore, the herein provided amino acid sequences enable means by which the isolation of either pre-bPL or bPL from bPL producing tissues (e.g. bovine placenta) or genetically engineered cells producing pre-bPL or bPL are both confirmed and facilitated. For example, various synthetic amino acid fragments or pre-bPL or bPL are made for use in generating bPL-specific antibodies useful in obtaining purified pre-bPL or bPL from living tissue or from genetically transformed cells engineered to produce bPL.

In one embodiment, bPL is isolated and purified from bovine placentas as described more fully in Example 1 below. It is important to note that the purification of bovine placental lactogen is complication by several factors. First, the concentration of bPL in bovine placentas is extremely low. Second, the isolation of bPL requires development of isolation techniques significantly different from those employed to isolate ovine and goat placental lactogens as bPL differs from these other placental lactogens in both size and physical/chemical properties. Additionally, due in part to the fact that bPL is a glycosylated protein, there exist multiple isoforms of bPL.

Once purified, the isolated bPL is then subjected to partial amino acid sequence analysis of the amino terminus of mature bPL and, due to the size of the bPL protein, limited sequence analysis of internal regions of the protein is also obtained. These amino acid sequences are then used to generate bPL-specific DNA probes for isolation of a bPL encoding DNA from which a complete amino acid sequence for bPL and pre-bPL is obtainable. Surprisingly, this approach led to the discovery of two distinct allelic forms of mature bPL and the heretofor not described precursor proteins therefor. The primary amino acid sequence of bPL, pre-bPL and allelic forms thereof are set forth in FIG. 1.

One skilled in the art will recognize that there may be substitutions or modifications in portions of the amino acid sequence that are not essential to biological activity of the bovine placental lactogen, and that substitutions or modifications may be made without materially adversely affecting biological activity. For instance, the mature bovine placental lactogen may optionally contain an N-terminal methionine which may result from production by expression in some recombinant systems. Additionally, amino acids may be modified so as to alter and/or eliminate certain or all glycosylation of the protein. Peptides having such substituted or modified amino acid sequences are considered to be equivalent to the peptides described herein as long as the essential bPL activity is retained.

Examples of means for determining bPL activity include, but are not limited to, assays which measure lactogenic (e.g. prolactin-like) activity of peptides and/or assays which measure growth hormone-like (e.g. somatotropin) activity of peptides. The lactogenic activity assays include, for example, those described by Buttle and Forsyth (1976), Byatt and Bremel (1986) and Shiu et al. (1973) which are incorporated by reference herein. The somatotropin-like assays include, for example, those described more fully hereinafter.

Briefly, in the lactogenic activity assays, mammary tissue is cultured in the presence of bPL or equivalent peptides and the degree of differentiation that occurs in the mammary tissue (measured histologically or by amount of milk specific markers, such as alpha-lactalbumin, lactose and/or casein, produced) is measured and compared with the degree of differentiation occurring following a similar incubation with known concentrations of prolactin. Specific examples of growth hormone-like activity assays are as described more fully in the Examples herein.

As previously discussed, having now obtained a primary amino acid sequence for bPL, DNA sequences coding for bPL and/or pre-bPL, useful in producing commercial quantities of bPL by recombinant DNA techniques, can be isolated or synthesized as described more fully herein. In one embodiment, described more fully in Example 2, below, cDNA sequences encoding bPL, pre-bPL and allelic forms thereof are isolated from a cDNA library created from messenger RNA obtained from bovine placental tissue. Specifically, as shown in FIG. 2, two cDNA clones, designated Clone A and Clone B, were isolated. DNA sequence analysis of said Clones A and B provided the complete DNA coding sequences for two allelic forms of pre- and mature bPL, part of the 5'-untranslated region of the bPL gene and all of the 3' untranslated region. The DNA sequences so obtained are set forth in FIG. 1.

Alternatively, given the primary amino acid sequence of bPL and pre-bPL taught herein, a plurality of DNA coding sequences can be constructed based upon the genetic code. Selection of the specific amino acid codons to be employed in generating a bPL or pre-bPL DNA coding sequence is generally guided by such factors as determining a sequence which will optimize transcription, translation and, ultimately, the amount of bPL protein produced in a chosen host cell. DNA sequences encoding bPL comprising the mature bPL protein alone or including the signal peptide ("pre") sequence can be made. The synthetic and/or isolated bPL cDNA clones are examples of DNA sequences which are employed to generate large quantities of bPL in genetically engineered cells.

Methods currently exist for expression of mammalian proteins, such as bPL, in such procaryotic hosts as *E. coli* and in such eucaryotic cells as yeast (e.g. *S. cerevisiae*) and mammalian cells (e.g. mouse C-127, bovine MDBK and CHO cells). As natural bPL is a glycosylated protein, eucaryotic cells are the preferred host. Yeast cells such as *S. cerevisiae* produce glycosylated proteins as do mammalian cells. The composition of the carbohydrate side chains, however, differ depending upon the host cell employed for protein production. Procaryotic cells typically yield non-glycosylated proteins and typically require a refolding of synthesized proteins to yield a biologically active form.

Production of bPL in both eucaryotic and procaryotic cells involves the insertion of bPL DNA coding sequences into conventional expression vectors. Examples of operable procaryotic expression vectors in such hosts as *E. coli*, Pseudomonas and Bacillus are well known in the art. Examples of operable eucaryotic expression vectors include, but are not limited to, the galactose (gal) promoter vectors in yeast (see Goff et al., 1984) and the bovine papilloma virus (BPV) vectors (see Howley et al., 1983) and dHFR vectors (see Subramani, et al., 1981) in mammalian cells.

While expression systems currently exist for production of desired proteins in both procaryotic and eucaryotic cells, the ability to produce active bPL by such means has heretofore not been demonstrated. It is known that the host cell employed in producing a given protein will impart its own unique glycosylation. These glycosylation patterns are not yet well characterized in either their composition or effect on the activity of molecules possessing the resultant altered glycosylation. Current dogma ascribes critical involvement of glycosylation in such properties as proper protein folding, internal protein clearance and interaction with biological receptors which mediate the action of such hormones as bPL. It was heretofore unknown what role, if any, the glycosylation pattern of bPL played in the biological activity of the protein.

The present invention now provides methods and compositions for producing active bPL in both glycosylated and non-glycosylated forms by recombinant DNA and chemical techniques. This discovery herein that both glycosylated and non-glycosylated synthetic forms of bPL are active is significant as it now opens the avenues of technology available for the commercial production of active, synthetic bPL. Indeed, preliminary isoelectric focusing analysis of bPL produced in mammalian cells, when compared to bPL isolated from bovine placenta confirms the expectation that recombinant bPL possess a different glycosylation pattern than native bPL yet, activity of the recombinantly produced bPL is maintained. Similarly, both deglycosylated bPL isolated from bovine placenta and bPL produced in such procaryotic hosts as *E. coli*, which bPL is produced in a non-glycosylated form, are active.

In one embodiment, bPL is produced in mouse C-127 cells employing a bovine papilloma virus (BPV) vector system essentially as described by Howley et al. (1983). Specifically, a DNA sequence coding for pre-bPL is inserted, by conventional recombinant DNA techniques, into a BPV expression vector which vector allows for production of bPL in cells transformed therewith. The BPV expression vector used in the production of mature bPL contained a promoter operable in the host cell chosen to produce bPL, a 5'-nontranslated region, a pre-bPL coding sequence and a mammalian cell transcription termination polyadenylation signal. In one embodiment, a mouse metallothionein promoter was employed along with an SV40 late polyadenylation sequence.

In one embodiment, the cDNA Clones A and B are first individually subcloned in a bacterial vector, such as pUC19, to generate multiple copies of said cDNA clones as follows. Specifically, Clones A and B are first individually subjected to partial digestion with the restriction enzyme EcoRI to yield 1350 and 1100 bp fragments, respectively, representing full length cDNA's encoding bPL. These 1350 and 1100 bp fragments are then gel purified and eluted from their respective gels in accordance with conventional procedures. The 1350 bp Clone A fragment and 1100 bp Clone B fragment are then individually inserted into the multiple cloning site of pUC19 previously digested with EcoRI in accordance with the recombinant DNA procedures described in Maniatis et al. (1982). The resultant chimeric plasmids, containing either the Clone A or Clone B fragment, are designated pMON3025 and pMON3023, respectively. The chimeric plasmids are then used to transform *E. coli* JM101 and the plasmids subsequently purified all in accordance with the general methods described in Maniatis et al. (1982). Those plasmids containing either the Clone A or Clone B fragment in the desired orientation are confirmed by restriction cleavage with an enzyme or enzymes cleaving at asymmetric sites. The bPL encoding sequences are then inserted into a BPV expression vector.

Conventional recombinant DNA techniques are employed to insert the bPL or pre-bPL DNA coding sequences into a BPV expression vector. In one embodiment, the purified pMON3025 plasmid is digested with HindIII and an approximately 1.2 kilobase (kb) fragment isolated by conventional methods. The dhimeric pMON3023 plasmid is handled in essentially the same manner as pMON3025. The HindIII ends are then converted to blunt-ends by methods described in Maniatis et al. (1982), BamHI linkers are added, and the bPL coding sequences are then inserted into a BPV vector containing a strong, host-specific promoter such as a metallothionein-I (MT-I) promoter (see Pavlakis and Hamer, 1983). Insertion of the DNA encoding pre-bPL is achieved by such methods as enzymatic or chemical ligation. The site of insert is selected so that the MT-I promoter will cause transcription of the DNA encoding bPL (e.g. structural gene). The correct orientation of the structural gene in the MT-I-containing BPV vector is ascertained by digestion with restriction enzymes cleaving at asymmetric internal restriction endonuclease sites. Mouse C-127 cells are then transfected with the chimeric BPV vectors essentially as described by Wigler et al. (1979) and transformants selected for by G418 (genticin) resistance essentially in accordance with methods described by Southern and Berg (1982). The transfected cells are then grown as described in Southern and Berg (1982) and production of bPL monitored by radio-immunoassay as described more fully in the examples herein. Use of such a mammalian cell expression system allows for production of correctly folded, glycosylated and biologically active bPL. Surprisingly, it was discovered that the allelic forms of bPL possess a differential activity profile in at least one in vitro biological assay.

Alternatively bPL can be produced in yeast cells. In one embodiment, bPL encoding DNA is inserted into yeast galactose (gal) promoter containing vectors described by Goff et al., (1984). Either the bPL signal ("pre") sequence is employed or a yeast signal peptide sequence such as alpha factor (see Kurjan and Herskowitz, 1982) is used in place of the bPL signal sequence. Specifically, the bPL Clone A or Clone B DNA's are individually cloned into a M13 vector essentially as described above. The chimeric M13 vectors are then subjected to oligonucleotide-directed site-specific mutagenesis essentially as described by Zoller and Smith (1982), Zoller and Smith (1983), and Norris et al. (1983), the relevant portions of which are herein incorporated by reference, to introduce an NcoI site before the first alanine or valine condon in the bPL coding sequence. The DNA sequence immediately preceding and adjacent to the alanine or valine codon is thus converted to the following sequence: 5'-CCATGG-3'. The chimeric M13 vectors are then individually digested with NcoI and HindIII to yield an approximately 800 bp bPL coding sequence which is gel purified, as previously described, and inserted into a yeast gal promoter vector containing the alpha-factor signal sequence, which yeast vector is previously digested with NcoI and HindIII. Yeast cells such as *S. cerevisiae* are then transformed with the chimeric yeast gal vectors as described by Ito et al., (1983). Transformants are selected by growth on leucine-deficient medium and bPL production monitored by radio-immunoassay as below.

Additionally, non-glycosylated forms of pre-bPL and/or bPL are produced by recombinant DNA techniques in such procaryotic systems as bacteria. In one embodiment, production of a non-glycosylated form of bPL is achieved in *E. coli* as follows. Plasmid pMON3023, described above, is digested with BamHI and Hind III to release an approximately 870 base pair (bp) fragment comprising a complete DNA sequence coding for mature bPL. The isolated 870 bp fragment is then shotgun cloned into M13mp9 previously digested with BamHI and Hind III. The chimeric M13mp9 vectors containing the bPL coding sequences are then subjected to oligonucleotide-directed site-specific mutagenesis using Amersham's (Arlington Heights, Ill.) Oligonucleotide-directed in vitro Mutagenesis System to create an NcoI site and add an initiator methionine at the amino terminus of the mature coding region and to increase the A-T content within the 5' end of the mature bPL coding sequence. The primers employed in the mutagenesis are either:

NcoI/METALA . . . mature bPL . . .
  5'-TCTTGTGCCAGGCCATGGCAGAAGATTATG CACCA-3' or

NcoI/METVAL . . . mature bPL . . .
  5'-TCTTGTGCCAGGCCATGGTGGAAGATTATG CACCA-3'.

Following successful mutagenesis, the modified mature bPL coding sequence is subcloned into an *E. coli* expression vector containing a recA promoter, a G10L translation enhancer sequence and T7 transcription terminator which vector is described in European Patent Application Publication No. 241,446 (published Oct. 14, 1987) which application is hereby incorporated by reference herein. A suitable *E. coli* host, such as *E. coli* strain W3110G, is then transformed with the expression vector containing the modified bPL coding sequence and the transformed cells are then cultured under conditions which cause expression of the bPL coding sequence all as essentially described in the above-referenced European Patent Application. The bPL protein produced by such transformed *E. coli* can then be purified by conventional methods for isolating proteins from such bacteria as *E. coli* or by methods analogous to those described in European Patent Application Publication No. 114,506 (published Aug. 1, 1984), and U.S. Pat. Nos. 4,599,197; 4,518,526; 4,511,502; 4,511,503; and 4,582,799, all incorporated herein by reference. The correct folding of *E. coli* produced bPL proteins can be achieved by dissolving the proteins in a suitable denaturant such as urea and then oxidizing the protein so that a biologically active configuration is achieved.

In another embodiment, non-glycosylated forms of bPL are produced enzymatically. Specifically, highly purified glycosylated bPL is treated with N-Glycanase (peptide-$N^4$ [N-acetyl-beta-glucosaminyl]_asparagine amidase) and/or O-Glycanase (endo-alpha-N-acetyl-galactosaminidase) to remove N-linked and O-linked oligosaccharides, respectively. The N-Glycanase and O-Glycanase can be obtained from Genzyme Corp. (Boston, Mass.). It was discovered herein that enzymatic removal of the oligosaccharides on bPL did not appreciably diminish the activity of bPL. Indeed, removal of the N-linked oligosaccharide may increase activity.

The pre-bPL and/or bPL produced and/or isolated in accordance with the methods and compositions of the present invention is now used to achieve the desired lactation enhancing and/or growth promoting effects in an animal by administration to an animal of an effective amount of pre-bPL and/or bPL.

In one embodiment, bPL is used to enhance growth of mammary parenchyma in cows by parenteral administration of said bPL to cows. For example, one method for parenteral administration of bPL is in accordance with the methods and compositions for intramammary infusion set forth in a concurrently filed U.S. patent application by Robert J. Collier and Michael F. McGrath entitled "Methods and Compositions for Enhancing Growth of Mammary Parenchyma", attorney docket number 37-21(5734)A, commonly assigned to Monsanto Company. For example, bPL is administered to, preferably, non-lactating cows or heifers during gestation or between the onset of puberty and the cows' first gestation by mammary infusion through the streak canal of each test. Infusions are given daily or on alternating days preferably over a period of a number of weeks from about 60 days prior to parturition. Doses of bPL so infused range from about 100 μg to about 200 mg per dose per quarter of gland with a preferred dose in the range of about 10 mg to about 200 mg per dose per quarter of gland and a most preferred dose of about 10 mg to about 100 mg per dose per quarter of gland. Total treatment amounts over any one treatment cycle ranges from about 100 μg to about 500 mg with a preferred range of about 50 mg to about 100 mg.

Alternatively, the bPL of the present invention is administered subcutaneously or intramuscularly to cows by injection, infusion or implantation in polymers or other media known to achieve the delivery of a required dosage in the circulatory system. Pharmaceutically acceptable base formulations such as solutions, emulsions or gels may be used, either encapsulated or not. These formulations may contain a single bPL isoform or mixtures thereof. Dosages may range from at least about 0.005 mg to about 200 mg per animal per day or more and preferably from about 5 mg to about 40 mg per animal per day. The amount most effective for achieving the desired biological effect is determined by routine experimentation. The actual preferred dosage of bPL is dependent on such variables as the size, general health, nutritional status of the specific animal and reproductive condition.

EXAMPLES

Materials and Methods

All oligonucleotides are synthesized employing an Applied Biosystems DNA Synthesizer in accordance with the procedures set forth by the manufacturer, Applied Biosystems, Inc. (Foster City, Calif.). Unless otherwise noted, all specialty chemicals are obtained from Sigma (St. Louis, Mo.). Restriction enzymes and DNA modifying enzymes are obtained from New England Biolabs (Beverly, Mass.), New England Nuclear (Boston, Mass.) and Bethesda Research Laboratories [BRL] (Gaithersburg, Md.) and used in accordance with manufacturers' directions. The pUC8 and pUC9 plasmids are obtained from BRL (Gaithersburg, Md.).

Q-Sepharose, Sephadex G-75 and Sephadex G-50 superfine are obtained from Pharmacia (Piscataway, N.J.). Amicon GH 25 is obtained from Amicon Corp. (Danvers, Mass.). Brownlee C18 columns are obtained from Brownlee Laboratories (Santa Clara, Calif.). Acetonitrile is obtained from Burdick and Jackson (Muskegen, Mich.). A Perkin-Elmer LC1-100 Laboratory Computing Integrator and a Series 4 Liquid Chromatograph are obtained from Perkin-Elmer (Norwalk, Conn.). Iodogen is obtained from Pierce Chemical Co., (Rockford, Ill.) and used in accordance with the procedure described below. Normal rabbit serum and goat anti-rabbit serum were obtained from Biotek Research (Shawnee Mission, Kans.).

Amino acid sequencing of bovine placental lactogen (bPL) and/or peptide fragments thereof, was performed on an Applied Biosystems Model 470A Protein Sequencer (Applied Biosystems, Inc., Foster City, Calif.) in accordance with the methods described by Hunkapiller et al. (1983). The respective phenylthodantoin (PTH)-amino acid derivatives are identified by reversed-phase high-performance liquid chromatography in an on-line fashion employing an Applied Biosystems, Inc. (Foster City, Calif.) Model 120A PTH Analyzer fitted with a Brownleee (Brownlee Laboratories, Santa Clara, Calif.) 2.1 mm diameter PTH-C18 column. Unless otherwise noted all specialty chemicals were obtained from Sigma (St. Louis, Mo.). Restriction enzymes and DNA modifying enzymes were purchased from New England Biolabs (Beverly, Mass.), New England Nuclear (Boston, Mass.) or Bethesda Research Laboratories (BRL) (Gaithersburg, Md.) and used in accordance with manufacturer's directions. T4 DNA Ligase was purchased from Promega Biotec (Madison, Wis.) and used in accordance with manufacturer's specifications. $^{32}$P-labeled nucleotides and $I^{125}$-labeled labeled protein A were purchased from Amersham (Arlington Heights, Ill.). Vectors M13mp9 and pUC19 were obtained from BRL (Gaithersburg, Md.). All bacterial growth media components and antibiotics were obtained from either Sigma (St. Louis, Mo.) or Difco Laboratories (Detroit, Mich.).

The growth media for the E. coli and conditions for selection of bacteria cells carrying plasmids containing an ampicillin resistance (amp$^r$) marker were as described in Maniatis et al. (1982). When employed for protein expression, E. coli were grown in Luria Broth (LB) or M9 minimal medium (Maniatis et al., 1982) supplemented with 100 μg/ml ampicillin. Transformation of E. coli host cells with recombinant vectors was performed as described in Maniatis et al. (1982).

Bovine placental lactogen produced by recombinant E. coli host cells was isolated and purified as follows. The recombinant E. coli cells are homogenized using Ultra-Turrax (Tekmar, Co., Cincinnati, Ohio). The cells are then lysed by passage through pre-cooled Manton Gaulin (APV Gaulin, Everett, Mass.) three times at 7000–9000 psi and then centrifuged at 25,000 rpm for 20 minutes at 4° C. The isolated pellets are rinsed and homogenized as previously described and urea added to a final concentration of 4.5 M urea. The pH is then adjusted to 11.3 with NaOH and the bPL protein allowed to refold for about 2½ days at 4° C. while stirring. The mixture is then centrifuged at 25,000 rpm for 30 min. at 4° C. and the supernatant subjected to reverse phase HPLC on a C-8 column (Alltech Assoc., Deerfield, Ill.). The bPL is eluted from the column using a gradient of 45–60% (v/v) acetonitrile containing 0.1% (v/v) TFA.

Radioimmunoassay for bPL was performed as follows: Antiserum for this assay, USDA-bPL-F56, is provided by D. J. Bolt, U.S.D.A., Beltsville, Md. as was the highly purified bPL used for radioiodination. The bPL is radioiodinated using an Iodogen method essentially as described by Salacinski et al. (1981). Specifically, 1 μg of Iodogen is dried to the walls of a glass test tube. To this is added 10 μg bPL in 0.5M Na phosphate buffer, pH 7.6 (30 μl) and 10 μCi Na [$^{125}$I]. The reaction was allowed to proceed for 10 min. at room temperature. The radioiodinated bPL is separated from free radioiodine on a 0.75×25 cm column of Sephadex G50. Antiserum (100 μl) diluted 1/5000 in assay buffer (40 mM sodium phosphate, 40 mM NaCl, 10 mM EDTA, 0.1% NaN$_3$ (w/v), 0.125% gelatin (w/v), pH 7.3) is added to 200 μl of diluted sample or standards (0.1–100 ng/tube) plus 200 μl radioiodinated bPL (about 1 ng/tube). Tubes are incubated at room temperature for 2.5–3 hours before addition of normal rabbit serum (100 μl) and goat anti-rabbit serum (100 μl). The tubes are incubated for at least six hours before precipitate is sedimented by centrifugation (3,500×g for 20 min.). The supernatant is aspirated and the tubes counted in a gamma counter.

Activity of recombinantly produced bPL was measured by a bovine liver radioreceptor assay as follows. A crude membrane preparation containing somatotropin receptors was prepared from 5–7 month pregnant cow liver using the method of Haro et al. (1984). The radioreceptor assay was carried out as follows: 100 μl of sample or recombinant bovine somatotropin (bST) standard was added to 200 μl of assay buffer (25 mM Tris-HCl, 10 mM CaCl$_2$, 0.1% (w/v) BSA, pH 7.6) in 13×100 mm polystyrene assay tubes. To this was added 100 μl [$^{125}$I]bST [approximately 100,000 cpm/tube, specific activity 60–100 μCi/μg, radioiodinated by a lactoperioxidase procedure described by Haro et al. (1984)] and 100 μl resuspended liver membrane preparation (4–6 mg/ml). Tubes were incubated overnight at room temperature with constant agitation. The assay was terminated by the addition of ice cold assay buffer (2 ml) followed by centrifugation at 2000×g for 30 min. at room temperature. The supernatant was aspirated and the pellet counted on a gamma counter. Activity is indicated by the ability of bPL to compete with [$^{125}$I]bST for the liver binding sites from the 100,000×g membranes at 25° C., pH 7.6 for 24 hours. Affinity of receptor binding is determined by conventional methods.

Alternatively, the somatotropin-like activity of placental purified and recombinantly produced bPL is determined in 3T3-L1 adipocytes by measuring the inhibition of insulin-stimulated [$^{14}$C]-glucose incorporation into lipids. The anti-insulin activity of bPL was compared against the activity of bovine somatotropin standards. The assay is based on the finding that glucose utilization in 3T3-L1 adipocytes is regulated in a reciprocal fashion by insulin and somatotropin. Somatotropin can directly inhibit, in a dose-dependent fashion, up to 50% of insulin-stimulated [$^{14}$C]-glucose incorporation into lipids. Insulin (Regular Iletin®, 100 units/cc) was purchased from Eli Lilly, Inc., Indianapolis, Ind. Bovine pituitary somatotropin and recombinant bovine somatotropin were purchased from Dr. A. F. Parlow, Harbor-U.C.L.A. Medical Center, Torrence, Calif. All cell culture procedures were performed under sterile conditions and represent modifications to procedures originally described in Reed and Lane (1980) and Schwartz (1984). Stock cultures of 3T3-L1 cells (American Type Culture Collection, Rockville, Md. ATCC CCL 92.1) were grown in 100 mm tissue culture dishes (Falcon, Oxnard, Calif.) in culture medium [Dulbecco-Vogt modified Eagle's medium with 4.5 g/L glucose (high glucose DME) containing 10% (v/v) bovine calf serum, 100 units/ml penicillin, 100 μg/ml streptomycin and 2 mM L-glutamine (all five from Gibco, Grand Island, N.Y.)] and in a humidified atmosphere composed of 7.5% CO$_2$ and 92.5% air at 37° C. Exponentially growing stock cultures of cells were subcultured every 3 to 4 days to prevent them from becoming confluent. To subculture the cells, medium was removed by aspiration, and the cell layer was rinsed twice with Ca$^{2+}$- and Mg$^{2+}$-free Dulbecco's phosphate buffered saline. The 3T3-L1 cells were incubated with a solution of 0.05% (w/v) trypsin and 0.02% (w/v) EDTA in isotonic buffer (Gibco) for 5 to 10 minutes at 37° C. to remove them from the plastic dish. Dispersed cells were rinsed from the dish into centrifuge tubes using culture medium and subjected to centrifugation at 150×g for 5 minutes at 22° C. The cell pellet was resuspended in fresh culture medium and inoculated into either fresh (100 mm dishes at 3.8 to 7.6×10$^2$ cells/cm$^2$/10 ml medium, or into 60 mm dishes (Falcon) at 3.0 to 5.0×10$^3$ cells/cm$^2$/4 ml medium/dish for experiments. Conversion of 3T3-L1 cells to adipocytes was initiated by adding 2.5 ml of differentiation medium [high glucose DME containing 2 μg/ml insulin, 0.5 mM 1-methyl-3-isobutylxanthine (Sigma, St. Louis, Mo.), 25 nM dexamethasone (Sigma), 100 units/ml penicillin, 100 μg/ml streptomycin, 2 mM L-glutamine, and 10% (v/v) fetal bovine serum (Gibco)] to 48–72 hour post-confluent cultures. Differentiation medium was removed by aspiration after 48 hours of incubation at 37° C. and incubation of the cells was continued in 2.5 ml culture medium containing 10% (v/v) fetal bovine serum in place of bovine calf serum for an additional 72 hours. Phase contrast microscopic examination of the cultures routinely showed 70% to 95% conversion of the cells into adipocytes. The culture medium was replaced with 2.5 ml serum-free medium [low glucose DME (1 g/L glucose) containing 1% (w/v) bovine serum albumin (Sigma #A-6003), 100 units/ml penicillin, 100 μg/ml streptomycin and 2 mM L-glutamine] 20 to 24 hours prior to experiments [see Glenn et al. (1988)].

The desired concentrations of hormones (e.g. insulin, somatotropin, bPL) were added to monolayers of converted cells in 2.5 ml of serum-free medium. Six hours after addition of hormones to the cells, 0.25 μCi of uniformly labeled D-[$^{14}$C]glucose was added to each culture in 100 μl of serum-free medium and the cells incubated at 37° C. for 18 hr. Incorporation of D-[$^{14}$C]glucose into lipids was stopped by complete aspiration of the medium, followed immediately by addition of 2.0 ml of Dole's reagent [78% (v/v) isopropyl alcohol, 20% (v/v) HPLC grade n-heptane, and 2% (v/v) 1.0 NH$_2$SO$_4$] Dole and Meinertz (1980) and incubation at 22° C. for 15 minutes to dissolve the cell layer. The solubilized cell layer was suspended by repeated pipetting of the extraction buffer over the surface of the dish with a glass Pasteur pipette. This mixture was transferred to 16×100 mm borosilcate glass screw-capped tubes and an additional 2.0 ml Dole's reagent was used to rinse each plate and pooled with the first extract. To each tube of extract, 1.75 ml water and 1.75 ml n-heptane were added, and the tubes were vortex mixed. Following separation of the organic and aqueous solvent phases, 2.0 ml of the upper organic phase were transferred to a scintillation vial, 5.0 ml Ready-Solv™ (Beckman Instruments, Inc., Palo Alto, Calif.) were added to each vial, and radioactivity in each sample was measured using a Beckman liquid scintillation counter.

Induction of transcription from the recA promoter was conducted briefly as follows. Overnight cultures of E. coli host cells carrying expression plasmids were diluted to 20–25 Klett units (measured with a Klett-Summerson meter using a green filter, Klett Mfg. Co., New York, N.Y.) in M9 minimal media supplemented with 0.25% (w/v) glucose and 1% (w/v) casamino acids and 0.25 μg/ml thiamine and grown to a cell density of 150–180 Klett units. The cells were then induced by adding nalidixic acid to the growth media at a final concentration of 50 μg/ml. Growth was continued for several hours at 37° C. with aliquots taken at 2 or 3 hours after induction for heterologous protein analysis. A high level of aeration was maintained throughout the growth in order to achieve maximal production of the desired gene product.

EXAMPLE 1

Isolation and Purification of Bovine Placental Lactogen from Fetal Bovine Placents Placentas are obtained from 6–8 month pregnant beef cows. A lysate of the granule enriched fraction (GEF) from the fetal placentomas is prepared as described by Byatt et al. (1986).

Bovine placental lactogen (bPL) is purified from the GEF lysate by modification of the procedure described by Byatt et al. (1986). Specifically, 50 ml of GEF lysate is loaded onto a column of Sephadex G-75 superfine (5×100 cm) and eluted with 20 mM Bis-Tris-HCl buffer, pH 6.5, at 120 ml/hr. Fractions containing bPL, determined by radioimmunoassay, from three G-75 runs are pooled and loaded onto a column of Q-Sepharose (3.2×13.5 cm) and eluted with NaCl 0-250 mM, in 20 mM Bis-Tris-HCl buffer, pH 6.5 at 180 ml/hr. bPL containing fractions which eluted at about 100 mM NaCl are pooled, and trifluoroacetic acid (TFA) added to 20 mM. 100 ml of the bPL containing Q-Sepharose fractions are loaded onto a Vydac C4 column (10–15 angstrom pore size, 5 μm particle size, 10×250 mm) at 6 ml/min, the column is then equilibrated at 40% (v/v) acetonitrile, 20 mM TFA for 5 minutes. An acetonitrile gradient from 40–50% (v/v) over 30 minutes is used to elute bPL. The acetonitrile is at 50% (v/v) for five minutes before the concentration is raised to 70% (v/v) to wash remaining protein off the column. Gel filtration (Amicon GH25, 2.8×25 cm column) is used to exchange acetonitrile/TFA, in the bPL containing fractions from the reverse phase step for 25 mM histidine-HCl, pH 6.3. Forty to 50 ml of this material (containing approximately 1–2 mg protein) is loaded onto a mono-P column (Pharmacia, Piscataway, N.J.) equilibrated with 25 mM histidine-HCl, pH 6.3. The isoforms of bPL are eluted with poly-buffer 75 (diluted 1/12) pH 4.0 at 0.5 ml/min. Fractions comprising each of the three major isoforms of bPL are pooled, diluted to 20 ml with water and TFA added to 20 mM. Each fraction is then loaded at 1 ml/min onto a Brownlee C18 column (300A pore size, 7 μm particle size, 2.1×30 mm). The column is equilibrated with 20% (v/v) acetonitrile, 20 mM TFA for 5 minutes at 1 ml per minute. The bPL is then eluted with an acetonitrile gradient from 20–50% (v/v) over 15 minutes with a five minute hold at 50% (v/v). The bPL peak is collected manually and stored at −20° C.

The mass of purified bPL is estimated from a protein standard such as porcine somatotropin. Known amounts of somatotropin (0.5–5 μg) are loaded onto a Brownlee C18 column (2.1×20 mm) and eluted with an acetonitrile gradient, 20–50% (v/v), over 5 minutes. The area under the peak is calculated using the Perkin-Elmer (Norwalk, Conn.) LCl-100 Laboratory Computing Integrator. A sample of bPL (of unknown concentration) is then run and the peak area calculated. The concentration of bPL is calculated by extrapolation from the somatotropin standard curve.

Prior to N-terminal sequence analysis of the bPL, an aliquot of bPL containing about 10×100 μg protein is transferred to a teflon tube and the solvent removed on a Speed Vac Concentrator (Savant, Farmingdale, N.Y.). The bPL is then redissolved in about 100 μl of 30% (v/v) acetonitrile. Amino acid sequence information on the bPL so isolated and purified is obtained for the N-terminal region and a number of internal trypsin and V8 protease generated peptides. The complete amino acid sequence of the mature bPL protein and signal peptide region are determined to be as previously described and as shown in FIG. 1. No differences in amino acid sequences for the bPL isoforms are found in the regions of the isoforms sequenced. The bPL protein is also determined to contain both N- and O- linked glycosylation.

EXAMPLE 2

Identification of a cDNA Coding for Bovine Placental Lactogen

Two 45-base long (45-mers) oligonucleotides, designated bPLII and bPLIII are designed to code for an internal sequence and N-terminal sequence of bPL, respectively. The nucleotide sequences of bPLII and BPLIII 45-mers are as follows:

bPLIII:
3'-CGGCTCCTGATGCGGGGGATGACGTTCTTG GTCGGGCCGTTGACG-5' bPLII:
3'-TGGGGGTTGTTGTTCCTCCGGCGGCGGTTGTGG CTCCTGCTCCGG-5'

Messenger RNA (mRNA) is prepared in accordance with the procedure described in Chirgwin, et al. (1979) from seven month pregnant bovine placenta and a λgt10 cDNA library prepared in accordance with the procedures described by Okayama and Berg (1982) and Gubler and Hoffman (1983) using reagents purchased from Stratagene (San Diego, Calif.). The λgt10 library is screened using the bPLII and bPLIII oligonucleotide probes in accordance with procedures described by Ullrich et al. (1984) and two positive clones designated Clone A and Clone B, are chosen for further analysis. Partial restriction maps of the two clones were determined to be as shown in FIG. 2.

As noted in the description of FIG. 2, the directional arrows underneath the partial restriction maps of Clones A and B denote the regions of the clones for which DNA sequence information was obtained.

DNA sequencing is performed using a Sequenase™ kit obtained from United States Biochemical Corp. (Cleveland, Ohio). The nucleotide sequence of the clones A and B are determined to be identical for all regions of sequence overlap.

The complete DNA coding sequence for bPL (mature protein and signal peptide region) is determined to be as shown in FIG. 1. The presence of a poly-A tail on the cDNA indicates that a full-length clone at the 3'-end is obtained. An inframe stop codon is found to occur 72 base pairs (bp) upstream from the initiation methionine. The mature bPL protein is found to begin with the sequence:

X-Glu-Asp-Tyr-Ala-Pro-Tyr-Cys-Lys-Asn . . . ,
wherein X is either Ala or Val, consistent with the N-terminal amino acid sequence determined for bPL isolated and purified as described in Example 1 herein. Furthermore, the sequence indicates that the bPL protein contains one N-linked glycosylation site, denoted by the hatched box in FIG. 1, has at least one O-linked glycosylation site, six cysteine and two tryptophan residues (similar to prolactin) and shares an approximate 50% homology in amino acid sequence with bovine prolactin and only about a 25% homology with bovine somatotropin. The low level of DNA sequence homology (e.g. 25%) between bPL and bovine somatotropin is quite unexpected given the great similarities between the biological activities of bPL and bovine somatotropin.

EXAMPLE 3

Production of bPL in *E. coli*

Plasmids pMON3023 and pMON3025, described above, comprising, respectively, a pUC19 vector having inserted therein at the multiple cloning site the cDNA encoding the valine or alanine allelic form of bPL, were individually subcloned into M13mp9. As previously described, the bPL coding sequences were then subjected to oligonucleotide-directed site-specific mutagenesis to introduce an NcoI site and a methionine codon at the N-terminus of the respective bPL structural genes (e.g. mature bPL coding sequence) and to increase the A–T content of the N-terminal portions of the bPL coding sequences. Following successful mutagenesis, the modified bPL coding sequences were then individually isolated from the M13mp9 vectors as NcoI-Hind III fragments and individually inserted into pBR327 plasmids containing an *E. coli* recA promoter, a G10L sequence and T7 transcription termination sequence as described in European Patent Application Publication Number 241,446 (published Oct. 14, 1987). The resultant chimeric expression vectors were designated pMON3068 and pMON3069 which vectors contained the coding sequences for the alanine and valine allelic forms of bPL, respectively. *E. coli* strain W3220G was then transformed with either pMON3068 or pMON3069 and cultured, as described above, under conditions which cause expression of the bPL coding sequences and, hence, production of bPL by the transformed *E. coli*. The *E. coli* produced alanine variant bPL was then isolated, purified and refolded as described above, and subjected to activity analysis using the above-described bovine liver radioreceptor assay.

Surprisingly, the *E. coli* produced alanine-bPL, which bPL is produced as a non-glycosylated protein, was active in the bovine radioreceptor assay.

EXAMPLE 4

Production of bPL in C127 Mouse Cells

Plasmids pMON3023 and 3025, previously described, were individually digested with Hind III and respective fragments of approximately 900 base pairs (bp) and 1.26 kb purified. These purified fragments contained all of the coding region for pre-bPL and no longer contained the natural bPL polyadenylation signal or part of the 3' untranslated region. The ends of the respective fragments were then filled in using T4 DNA polymerase to create blund ends. BamHI linkers were then ligated to the ends of the respective fragments and the fragments then digested with BamHI to produce BamHI fragments of approximately 890 bp and 1.23 kb in length, respectively. The BamHI fragments containing either the valine or alanine allelic coding sequence were then cloned into a bovine papilloma virus (BPV) vector containing a mouse metallothionein (mMT) promoter and SV40 late polyadenylation site so that the mMT promoter controls the transcription of the bPL coding sequence.

Three cell lines, mouse C127, baby hamster kidney and mouse NIH 3T3 cells were then co-transfected with the chimeric bPL-containing BPV vector and a SV2neo vector as described by Wigler et al. (1979) and transformants selected for G418 resistance. The isolated colonies were expanded and production of bPL monitored by radioimmunoassay as described above.

The alanine and valine allelic forms of bPL produced in the recombinant C127 cells were then assayed for the presence of bPL activity in the radioreceptor assay essentially as described above. Specifically, culture media from C127 cells transfected with either the alanine or the valine variant of bPL was sequentially diluted and the dilution curve was compared with that produced by sequential dilutions of native bPL purified from placenta. Both allelic forms of recombinantly produced bPL showed an ability to displace [$^{125}$I]bST and therefore bind specifically to the somatotropin receptor. Furthermore, the dilution curve for the valine bPL variant was determined to be steeper than the dilution curves for both native purified bPL and the alanine bPL variant (e.g. allelic form). The difference in the slopes of the dilution curves indicates that the affinity of the somatotropin receptor was greater for the valine variant than for both the native bPL and alanine variant. The greater binding affinity exhibited by the valine allelic form, as compared to the alanine form, is presumed to be indicative of an ability of the valine allelic form to provide a greater potentiation of growth hormone related to bPL activity.

The ability to produce substantially pure forms of the individual bPL allelic variants is therefore a significant discovery as it provides for the potential of achieving both greater and more specific biological responses in recipient animals.

The alanine and valine allelic forms of bPL produced in the recombinant C127 cells were also assayed for somatotropin-like activity in the 3T3-L1 adipocyte assay as described above. The results of this assay showed that both recombinant forms of bPL inhibited [$^{14}$C]-glucose incorporation at doses equivalent to somatotropin. The amount of inhibition, however, was slightly reduced as compared to the amount of inhibition observed for somatotropin.

The foregoing examples illustrate preferred embodiments of this invention and are not intended to limit the invention's scope in any way. While this invention has been described in relation to its preferred embodiments, various modifications thereof will be apparent to one skilled in the art from reading this application.

The relevant portions of the following references are hereby incorporated by reference:

Arima et al. (1983) Endocrinology 113: 2186–2194.

Buttle, H. L. and Forsyth, I. A. (1976) J. Endocrin. 68:141–146.

Byatt, J. C. and Bremel, R. D. (1986) J. Dairy Sci. 69:2066–2071.

Byatt et al. (1986) Endocrinology 119: 1343–1350.

Chirgwin, J. M. et al. (1979) Biochemistry 18:5294–5299.

Dole, V. P. and Meinertz, H. (1980) J. Biol. Chem. 235:2595–2599.

Eakle et al. (1982) Endocrinology 110: 1758–1765.

Glenn, K. C. et al. (1988) J. Cell. Biochem. 37:371–384.

Goff, C. G. et al. (1984) Gene 27: 35–46.

Gubler, W. and Hoffman, B. (1983) Gene 2: 5263–5269.

Haro et al. (1984) Mol. Cell. Endocrinol. 38:109–116.

Howley, P. M. et al. (1983) Methods in Enzymology 101:387.

Hunkapiller et al. (1983) Methods in Enzymology 91: 399–413.

Ito, H. et al. (1983) J. Bacteriology 153: 163–168.

Kurjan, J. and Herskowitz, I. (1983) Cell 30: 933–943.

Lehninger, A. L. (1976) *Biochemistry*, 2nd Ed. Worth Publishers, Inc., New York City, N.Y. pp. 72–75, 315–322.

Maniatis et al. eds. (1982) *Molecular Cloning: A Laboratory Manual,* Cold Spring Harbor Laboratory, Cold Spring Harbor, N.Y.

Murthy et al. (1982) Endocrinology 111: 2117–2124.

Norris et al. (1983) Nuc. Acids Res. 11: 5103–5112.

Okayama, H. and Berg, P. (1982) Mol. Cell Biology 2: 161–170.

Pavlakis, G. N. and Hamer, D. H. (1983) Recent Progress in Hormone Research 39: 353.

Reed, B. C. and Lane, M. D. (1980) Proc. Nat'l. Acad. Sci., U.S.A. 77:285–289.

Salicinski, P. R. P. et al. (1981) Analytical Biochemistry 117: 136–146.

Schwartz, J. (1984) Biochem. Biophys. Res. Comm. 125:237–243.

Shiu et al. (1973) Science 180:968.

Southern, P. J. and Berg, P. 91983) J. of Molecular and Applied Genetics 1: 327.

Subramani, S. et al. (1981) Molecular and Cellular Biology 1: 854.

Ullrich, A. et al. (1984) Embo. J. 3: 361–364.

Wigler, M. et al. (1979) Cell 16: 777.

Zoller and Smith (1982) Nuc. Acids Res. 10: 6487–6500.

Zoller and Smith (1983) Methods in Enzymology 100: 468–500.

What is claimed is:

1. A synthetic DNA molecule comprising a DNA sequence encoding a peptide having the following amino acid sequence, reading from the amino terminus to the carboxy terminus:

X-Glu-Asp-Tyr-Ala-Pro-Tyr-Cys-Lys-Asn-Gln-Pro-Gly-Asn-Cys-Arg-Ile-Pro-Leu-Gln-Ser-Leu-Phe-Glu-Arg-Ala-Thr-Leu-Val-Ala-Ser-Asn-Asn-Tyr-Arg-Leu-Ala-Arg-Glu-Met-Phe-Asn-Glu-Phe-Asn-Lys-Gln-Phe-Gly-Glu-Gly-Lys-Asn-Phe-Thr-Ser-Lys-Val-Ile-Asn-Ser-Cys-His-Thr-Glu-Phe-Met-Thr-Thr-Pro-Asn-Asn-Lys-Glu-Ala-Ala-Ala-Asn-Thr-Glu-Asp-Glu-Ala-Leu-Leu-Arg-Leu-Val-Ile-Ser-Leu-Leu-His-Ser-Trp-Asp-Glu-Pro-Leu-His-Gln-Ala-Val-Thr-Glu-Leu-Leu-His-Arg-Asn-Gly-Ala-Ser-Pro-Asp-Ile-Leu-Ala-Arg-Ala-Lys-Glu-Ile-Glu-Asp-Lys-Thr-Lys-Val-Leu-Leu-Glu-Gly-Val-Glu-Met-Ile-Gln-Lys-Arg-Val-His-Pro-Gly-Glu-Lys-Lys-Asn-Glu-Pro-Tyr-Pro-Val-Trp-Ser-Glu-Lys-Ser-Ser-Leu-Thr-Ala-Asp-Asp-Glu-Asp-Val-Arg-Gln-Thr-Ala-Phe-Tyr-Arg-Met-Phe-His-Cys-Leu-His-Arg-Asp-Ser-Ser-Lys-Ile-Ser-Thr-Tyr-Ile-Asn-Leu-Leu-Lys-Cys-Arg-Phe-Thr-Pro-Cys; wherein X is Ala, Val, Met-Ala or Met-Val.

2. The synthetic DNA molecule of claim 1 in which the DNA sequence comprises the following nucleotide sequence, reading from the 5' end to the 3' end:

CGCTCGCCCGCTCCCTCTCTCGCTCGCTTT
TTGTCTCTCGCGCTGCCTCTCCCCACCTCC
GATTTGCTACACTAAGGCTCCCGTCAA
TGGACTGCATTGAGAGCCGGCTCCGGC
GCGAGTGCCTCTCCGCTTCACGCTCGATTTCCA
GGCATTCTTCCCTTATTAAGTATTCGTGTAATA
TTAATAGTCATGAATATCTGCTATTAGGAG
GCTCCAGGAACGCTGCCCAGCGCGCTTATT
AGAAGCTCAAGCGAAGCCGCGGCTCAGAAA
AGAGGGGGAGACACGGATTAAGGAACACGC
GCGGTTGGGCCATCTCCCCATCAGCAGCAG
TCCTCATCCTGGGATTTCTCTCCAATCCTCATG
GCTCCAGCATCTAGCCATCGTGGGCACCAG
TGGATTTGTGACCTTGTTCGAGGGTCCTGCCTG
CTCCTGCTGCTGGTGGTGTCAAATCTACTC
TTGTGCCAGGGTGXGGAGGATTATGCACCA
TACTGTAAAAACCAACCTGGCAACTGCCGG
ATTCCCCTTCAAAGCCTGTTTGAGAGAGCA
ACATTGGTGGCTAGCAACAACTATAGGCTC
GCCAGGGAAATGTTCAATGAATTTAATAAA
CAGTTTGGCGAGGGCAAAAACTTCACTTCC
AAGGTCATCAACAGCTGCCACACCGAATTC
ATGACTACCCCTAAYAACAAAGAAGCAGCT
GCAAATACAGAGGACGAAGCCCTZTTGAGG
TTGGTTATCAGTTTGCTCCACTCGTGGGATGAA
CCTCTGCATCAGGCAGTCACAGAGTTGTTG
CACAGGAATGGAGCCTCACCTGATATCTTG
GCAAGGGCTAAAGAGATTGAGGACAAGACC
AAAGTACTTCTAGAAGGTGTGGAAATGATA
CAAAAAAGGGTTCATCCTGGAGAGAAGAAG
AACGAGCCCTATCCAGTGTGGTCAGAAAAG
TCCTCCCTGACAGCAGACGATGAGGATGTG
CGCCAAACTGCCTTTTATAGAATGTTCCAC
TGCCTACACAGGGATTCGAGTAAAATTAGC
ACCTACATCAATTTGCTTAAGTGCCGATTC
ACCCCATGCTAAGCCCACAATTAACCCAAC
CAGTCCTGAGATGGTTAGTGATGATCCATCCCG
TCAAAAGCTTCTTTGAGTTTTATAGCTCTTTAA
TYGCATGTTTGGGTGTAATGGGTTCTATCT
GAAACAAAATAAACACAGATTCTGTAGAGA
TGTCAAAATCTAAAAA;

wherein

X is T or C,

Y is T or C and

Z is A or G.

3. The synthetic DNA molecule of claim 2 in which X is T, Y is T and Z is A.

4. The synthetic DNA molecule of claim 2 in which X is C, Y is C and Z is G.

5. The synthetic DNA molecule of claim 1 in which the DNA sequence comprises the following nucleotides, reading from the 5' end to the 3' end:

GTTGGGCCATCTCCCCATCAGCAGCAGTTT
TCATCCTGGGATTTCTCTCCAATCCTCATGGCT
CCAGCATCTAGCCATCGTGGGCACCAGTGG
ATTTGTGACCTTGTTCGAGGGTCCTGCCTG
CTCCTGCTGCTGGTGGTGTCAAATCTACTC
TTGTGCCAGGGTGXGGAGGATTATGCACCA
TACTGTAAAAACCAACCTGGCAACTGCCGG
ATTCCCCTTCAAAGCCTGTTTGAGAGAGCA
ACATTGGTGGCTAGCAACAACTATAGGCTC
GCCAGGGAAATGTTCAATGAATTTAATAAA
CAGTTTGGCGAGGGCAAAAACTTCACTTCC
AAGGTCATCAACAGCTGCCACACCGAATTC
ATGACTACCCCTAAYAACAAAGAAGCAGCT
GCAAATACAGAGGACGAAGCCCTZTTGAGG
TTGGTTATCAGTTTGCTCCACTCGTGGGATGAA
CCTCTGCATCAGGCAGTCACAGAGTTGTTG
CACAGGAATGGAGCCTCACCTGATATCTTG
GCAAGGGCTAAAGAGATTGAGGACAAGACC
AAAGTACTTCTAGAAGGTGTGGAAATGATA
CAAAAAAGGGTTCATCCTGGAGAGAAGAAG
AACGAGCCCTATCCAGTGTGGTCAGAAAAG
TCCTCCCTGACAGCAGACGATGAGGATGTG
CGCCAAACTGCCTTTTATAGAATGTTCCAC
TGCCTACACAGGGATTCGAGTAAAATTAGC
ACCTACATCAATTTGCTTAAGTGCCGATTC
ACCCCATGCTAAGCCCACAATTAACCCAAC
CAGTCCTGAGATGGTTAGTGATGATCCATCCCG
TCAAAAGCTTCTTTGAGTTTTATAGCTCTTTAA
TYGCATGTTTGGGTGTAATGGGTTCTATCT
GAAACAAAATAAACACAGATTCTGTAGAGA
TGTCAAAATCTAAAAA;

wherein

X is T or C,

Y is T or C and

Z is A or G.

6. The synthetic DNA molecule of claim 5 in which X is T, Y is T and Z is A.

7. The synthetic DNA molecule of claim 5 in which X is C, Y is C and Z is G.

8. The synthetic DNA molecule of claim 1 in which the DNA sequence comprises the following nucleotides, reading from the 5' end to the 3' end:

GXGGAGGATTATGCACCATACTGTAAAAACCAA
CCTGGCAACTGCCGGATTCCCCTTCAAAGC
CTGTTTGAGAGAGCAACATTGGTGGCTAGC
AACAACTATAGGCTCGCCAGGGAAATGTTC
AATGAATTTAATAAACAGTTTGGCGAGGGC
AAAAACTTCACTTCCAAGGTCATCAACAGC
TGCCACACCGAATTCATGACTACCCCTAAYAAC
AAAGAAGCAGCTGCAAATACAGAGGACGAA
GCCCTZTTGAGGTTGGTTATCAGTTTGCTCCAC
TCGTGGGATGAACCTCTGCATCAGGCAGTC
ACAGAGTTGTTGCACAGGAATGGAGCCTCA
CCTGATATCTTGGCAAGGGCTAAAGAGATT
GAGGACAAGACCAAAGTACTTCTAGAAGGT
GTGGAAATGATACAAAAAAGGCTTCATCCT
GGAGAGAAGAAGAACGAGCCCTATCCAGTG
TGGTCAGAAAAGTCCTCCCTGACAGCAGAC
GATGAGGATGTGCGCCAAACTGCCTTTTATAGA
ATGTTCCACTGCCTACACAGGGATTCGAGT
AAAATTAGCACCTACATCAATTTGCTTAAG
TGCCGATTCACCCCATGCTAA;

wherein

X is T or C,

Y is T or C and

Z is A or G.

9. The synthetic DNA molecule of claim 8 in which X is T, Y is T and Z is A.

10. The synthetic DNA molecule of claim 8 in which X is C, Y is C and Z is G.

11. A synthetic DNA molecule comprising a DNA sequence coding for a peptide having the following amino acid sequence, reading from the amino terminus to the carboxy terminus:

Met-Ala-Pro-Ala-Ser-Ser-His-Arg-Gly-His-Gln-Trp-Ile-Cys-Asp-Leu-Val-Arg-Gly-Ser-Cys-Leu-Leu-Leu-Leu-Leu-Val-Val-Ser-Asn-Leu-Leu-Leu-Cys-Gln-Gly-X-Glu-Asp-Tyr-Ala-Pro-Tyr-Cys-Lys-Asn-Gln-Pro-Gly-Asn-Cys-Arg-Ile-Pro-Leu-Gln-Ser-Leu-Phe-Glu-Arg-Ala-Thr-Leu-Val-Ala-Ser-Asn-Asn-Tyr-Arg-Leu-Ala-Arg-Glu-Met-Phe-Asn-Glu-Phe-Asn-Lys-Gln-Phe-Gly-Glu-Gly-Lys-Asn-Phe-Thr-Ser-Lys-Val-Ile-Asn-Ser-Cys-His-Thr-Glu-Phe-Met-Thr-Thr-Pro-Asn-Asn-Lys-Glu-Ala-Ala-Ala-Asn-Thr-Glu-Asp-Glu-Ala-Leu-Leu-Arg-Leu-Val-Ile-Ser-Leu-Leu-His-Ser-Trp-Asp-Glu-Pro-Leu-His-Gln-Ala-Val-Thr-Glu-Leu-Leu-His-Arg-Asn-Gly-Ala-Ser-Pro-Asp-Ile-Leu-Ala-Arg-Ala-Lys-Glu-Ile-Glu-Asp-Lys-Thr-Lys-Val-Leu-Leu-Glu-Gly-Val-Glu-Met-Ile-Gln-Lys-Arg-Val-His-Pro-Gly-Glu-Lys-Lys-Asn-Glu-Pro-Tyr-Pro-Val-Trp-Ser-Glu-Lys-Ser-Ser-Leu-Thr-Ala-Asp-Asp-Glu-Asp-Val-Arg-Gln-Thr-Ala-Phe-Tyr-Arg-Met-Phe-His-Cys-Leu-His-Arg-Asp-Ser-Ser-Lys-Ile-Ser-Thr-Tyr-Ile-Asn-Leu-Leu-Lys-Cys-Arg-Phe-Thr-Pro-Cys; wherein X is either Ala or Val.

12. The synthetic DNA molecule of claim 11 in which the DNA sequence comprises the following nucleotides, reading from the 5' end to the 3' end:

GTTGGGCCATCTCCCCATCAGCAGCAGTCC
TCATCCTGGGATTTCTCTCCAATCCTCATGGCT
CCAGCATCTAGCCATCGTGGGCACCAGTGG
ATTTGTGACCTTGTTCGAGGGTCCTGCCTG
CTCCTGCTGCTGGTGGTGTCAAATCTACTC
TTGTGCCAGGGTGXGGAGGATTATGCACCA
TACTGTAAAAACCAACCTGGCAACTGCCGG
ATTCCCCTTCAAAGCCTGTTTGAGAGAGCA
ACATTGGTGGCTAGCAACAACTATAGGCTC
GCCAGGGAAATGTTCAATGAATTTAATAAA
CAGTTTGGCGAGGGCAAAAACTTCACTTCC
AAGGTCATCAACAGCTGCCACACCGAATTC
ATGACTACCCCTAAYAACAAAGAAGCAGCT
GCAAATACAGAGGACGAAGCCCTZTTGAGG
TTGGTTATCAGTTTGCTCCACTCGTGGGATGAA
CCTCTGCATCAGGCAGTCACAGAGTTGTTG
CACAGGAATGGAGCCTCACCTGATATCTTG
GCAAGGGCTAAAGAGATTGAGGACAAGACC
AAAGTACTTCTAGAAGGTGTGGAAATGATA
CAAAAAAGGGTTCATCCTGGAGAGAAGAAG
AACGAGCCCTATCCAGTGTGGTCAGAAAAG
TCCTCCCTGACAGCAGACGATGAGGATGTG
CGCCAAACTGCCTTTTATAGAATGTTCCAC
TGCCTACACAGGGATTCGAGTAAAATTAGC
ACCTACATCAATTTGCTTAAGTGCCGATTC
ACCCCATGCTAAGCCCACAATTAACCCAAC
CAGTCCTGAGATGGTTAGTGATGATCCATC
CCGTCAAAAGCTTCTTTGAGTTTTATAGCTCTT
TAATYGCATGTTTGGGTGTAATGGGTTCTATCT
GAAACAAAATAAACACAGATTCTGTAGAGA
TGTCAAAATCTAAAAA;

wherein
X is T or C,
Y is T or C and
Z is A or G.

13. The synthetic DNA molecule of claim 12 in which X is T, Y is T and Z is A.

14. The synthetic DNA molecule of claim 12 in which X is C, Y is C and Z is G.

15. The synthetic DNA molecule of claim 11 in which the DNA sequence comprises the following nucleotides, reading from the 5' end to the 3' end:

CGCTCGCCCGCTCCCTCTCTCGCTCGCTTT
TTGTCTCTCGCGCTGCCTCTCCCCACCTCC
GATTTGCTACACTAAGGCTCCCGTCAATGG
ACTGCATTGAGAGCCGGCTCCGGCGCGAGT
GCCTCTCCGCTTCACGCTCGATTTCCAGGC
ATTCTTCCCTTATTAAGTATTCGTGTAATA
TTAATAGTCATGAATATCTGCTATTAGGAG
GCTCCAGGAACGCTGCCCAGCGCGGTTATT
AGAAGCTCAAGCGAAGCCGCGGCTCAGAAA
AGAGGGGGAGACACGGATTAAGGAACACGC
GCGGTTGGGCCATCTCCCCATCAGCAGCAG
TCCTCATCCTGGGATTTCTCTCCAATCCTCATG
GCTCCAGCATCTAGCCATCGTGGGCACCAG
TGGATTTGTGACCTTGTTCGAGGGTCCTGCCTG
CTCCTGCTGCTGGTGGTGTCAAATCTACTC
TTGTGCCAGGGTGXGGAGGATTATGCACCA
TACTGTAAAAACCAACCTGGCAACTGCCGG
ATTCCCCTTCAAAGCCTGTTTGAGAGAGCA
ACATTGGTGGCTAGCAACAACTATAGGCTC
GCCAGGGAAATGTTCAATGAATTTAATAAA
CAGTTTGGCGAGGGCAAAAACTTCACTTCC
AAGGTCATCAACAGCTGCCACACCGAATTC
ATGACTACCCCTAAYAACAAAGAAGCAGCT
GCA AATACAGAGGACGAAGCCCTZ TTGAGG
TTGGTTATCAGTTTGCTCCACTCGTGGGAT
GAACCTCTGCATCAGGCAGTCACAGAGTTG
TTGCACAGGAATGGAGCCTCACCTGATATC
TTGGCAAGGGCTAAAGAGATTGAGGACAAG
ACCAAAGTACTTCTAGAAGGTGTGGAAATG
ATACAAAAAAGGGTTCATCCTGGAGAGAAGA
AGAACGAGCCCTATCCAGTGTGGTCAGAAA
AGTCCTCCCTGACAGCAGACGATGAGGATG
TGCGCCAAACTGCCTTTTATAGAATGTTCC
ACTGCCTACACAGGGATTCGAGTAAATTTA
GCACCTACATCAATTTGCTTAAGTGCCGAT
TCACCCCATGCTAAGCCCACAATTAACCCA
ACCAGTCCTGAGATGGTTAGTGATGATCCA
TCCCGTCAAAAGCTTCTTTGAGTTTTATAG
CTCTTTAATYGCATGTTTGGGTGTAATGGG
TTCTATCTGAAACAAAATAAACACAGATTCTGT
AGAGATGTCAAAATCTAAAAA;

wherein
X is T or C,
Y is T or C and
Z is A or G.

16. The synthetic DNA molecule of claim 15 in which X is T, Y is T and Z is A.

17. The synthetic DNA molecule of claim 15 in which X is C, Y is C and Z is G.

18. A genetically transformed cell comprising the synthetic DNA molecule of claim 1.

19. A genetically transformed cell comprising the synthetic DNA molecule of claim 11.

20. The genetically transformed cell of claim 18 or 19 in which the cell is selected from a group consisting of bacteria, yeast and mammalian cells.

21. The genetically transformed cell of claim 18 or 19 in which the cell is *E. coli*.

22. The genetically transformed cell of claim 18 or 19 in which the cell is a mouse C127 cell.

23. A method for producing bovine placental lactogen comprising causing expression of a gene in a transformed cell, said gene comprising the synthetic DNA sequence of claim 1 or 11, coding for bovine placental lactogen and obtaining the bovine placental lactogen produced in the transformed cell.

24. The method of claim 23 in which the transformed cell is selected from a group consisting of a bacteria, a yeast and a mammalian cell.

25. The method of claim 24 in which the bacteria is a Gram-negative bacteria.

26. The method of claim 25 in which the Gram-negative bacteria is *E. coli*.

* * * * *